(12) United States Patent
Bonadio et al.

(10) Patent No.: US 6,623,426 B2
(45) Date of Patent: Sep. 23, 2003

(54) LAPAROSCOPIC SEALED ACCESS DEVICE

(75) Inventors: Frank Bonadio, Bray (IE); Ronan Bernard McManus, Bray (IE); Derek William Young, Blackrock (IE); Alan Reid, Clontarf (IE)

(73) Assignee: Atropos Limited, Wicklow (IE)

( * ) Notice: Subject to any disclaimer, the term of this patent is extended or adjusted under 35 U.S.C. 154(b) by 0 days.

(21) Appl. No.: 09/804,418

(22) Filed: Mar. 13, 2001

(65) Prior Publication Data

US 2001/0047188 A1 Nov. 29, 2001

Related U.S. Application Data

(63) Continuation of application No. PCT/IE99/00127, filed on Dec. 1, 1999.

(30) Foreign Application Priority Data

| Dec. 1, 1998 | (IE) | 980999 |
| May 24, 1999 | (IE) | 990416 |
| Feb. 15, 1999 | (IE) | 990107 |
| Feb. 15, 1999 | (IE) | 990108 |
| Feb. 15, 1999 | (IE) | 990110 |
| Feb. 15, 1999 | (IE) | 990112 |

(51) Int. Cl.$^7$ .............................................. A61B 1/32
(52) U.S. Cl. .................. 600/207; 600/206; 600/208; 604/513; 604/539; 606/108
(58) Field of Search .................. 606/1, 108; 604/513, 604/264, 539; 600/204, 206, 207, 208

(56) References Cited

U.S. PATENT DOCUMENTS 1,598,284 A  8/1926  Kinney
3,244,169 A  4/1966  Baxter ........................... 128/82
3,347,226 A  10/1967  Harrower
3,347,227 A  10/1967  Harrower
3,397,692 A  8/1968  Creager, Jr. et al.
3,522,800 A  8/1970  Lesser
3,797,478 A  3/1974  Walsh et al. .................... 128/1
3,915,171 A  10/1975  Shermeta .................... 128/348
4,228,792 A  10/1980  Rhys-Davies .............. 128/24.3

(List continued on next page.)

FOREIGN PATENT DOCUMENTS

DE  3739532  12/1988
DE  3737121 A1  5/1989
DE  29600939  6/1998

(List continued on next page.)

OTHER PUBLICATIONS

Original Specification of Application No. 09/804,552, filed Mar. 13, 2001.
Original Specification of Application No. 09/688,333, filed Oct. 16, 2000.

(List continued on next page.)

*Primary Examiner*—Linda C. M. Dvorak
*Assistant Examiner*—Jocelyn Ram
(74) *Attorney, Agent, or Firm*—Finnegan, Henderson, Farabow, Garrett & Dunner, LLP

(57) ABSTRACT

A hand access device for use as a seal for sealing a surgeon's forearm on entry through a wound opening, for example, in an abdominal wall contains a substantially tubular sleeve of pliable gas tight material. The tube is turned axially back on itself to define an outer sleeve section and an inner sleeve section which define therebetween a sealed inflatable chamber. The inner sleeve section is engaged by the forearm which, on insertion, causes the sleeve to evert. The device has eversion limiting means in the form of inner and outer rings which are of elastomeric material.

25 Claims, 9 Drawing Sheets

U.S. PATENT DOCUMENTS

| | | |
|---|---|---|
| 5,045,070 A | 9/1991 | Grodecki et al. |
| 5,158,553 A | 10/1992 | Berry et al. ............... 604/248 |
| 5,161,773 A | 11/1992 | Tower |
| 5,213,114 A | 5/1993 | Bailey, Jr. |
| 5,342,385 A | 8/1994 | Norelli et al. ............... 606/193 |
| 5,350,364 A | 9/1994 | Stephens et al. ............ 604/167 |
| 5,364,345 A | 11/1994 | Lowrey et al. |
| 5,366,478 A | 11/1994 | Brinkerhoff et al. ........ 660/213 |
| 5,391,156 A | 2/1995 | Hildwein et al. |
| 5,480,410 A | 1/1996 | Cuschieri et al. ........... 606/213 |
| 5,514,133 A | 5/1996 | Golub et al. .................. 606/1 |
| 5,522,791 A | 6/1996 | Leyva ......................... 600/207 |
| 5,524,644 A | 6/1996 | Crook ......................... 128/888 |
| 5,526,536 A | 6/1996 | Cartmill ...................... 2/161.7 |
| 5,545,179 A | 8/1996 | Williamson, IV ........... 606/213 |
| 5,634,911 A | 6/1997 | Hermann et al. ............ 604/256 |
| 5,634,937 A * | 6/1997 | Mollenauer et al. ........ 604/115 |
| 5,636,645 A * | 6/1997 | Ou .............................. 128/898 |
| 5,640,977 A | 6/1997 | Leahy et al. ................ 128/897 |
| 5,649,550 A | 7/1997 | Crook |
| 5,653,705 A | 8/1997 | de la Torre et al. ............ 606/1 |
| 5,672,168 A | 9/1997 | de la Torre et al. ............ 606/1 |
| 5,741,234 A | 4/1998 | Aboul-Hosn ................ 604/174 |
| 5,741,298 A | 4/1998 | MacLeod ..................... 606/213 |
| 5,803,921 A | 9/1998 | Bonadio ......................... 606/1 |
| 5,810,721 A | 9/1998 | Mueller et al. ............. 600/206 |
| 5,813,409 A | 9/1998 | Leahy et al. ................ 128/897 |
| 5,832,925 A | 11/1998 | Rothrum ..................... 128/849 |
| 5,853,395 A | 12/1998 | Crook et al. ................ 604/174 |
| 5,899,208 A | 5/1999 | Bonadio ...................... 128/897 |
| 5,906,577 A | 5/1999 | Beane et al. ................ 600/207 |
| 5,947,922 A | 9/1999 | MacLeod ...................... 604/27 |
| 5,957,913 A | 9/1999 | de la Torre et al. ............ 606/1 |
| 5,964,781 A | 10/1999 | Mollenauer et al. ........ 606/213 |
| 5,997,515 A | 12/1999 | de la Torre et al. ........ 604/256 |
| 6,033,426 A | 3/2000 | Kaji ........................... 606/213 |
| 6,033,428 A * | 3/2000 | Sardella ...................... 606/213 |
| 6,042,573 A | 3/2000 | Lucey ......................... 606/246 |
| 6,048,309 A | 4/2000 | Flom et al. |
| 6,077,288 A | 6/2000 | Shimomura et al. ........ 606/185 |
| 6,110,154 A | 8/2000 | Shimomura et al. ........ 604/256 |
| 6,142,935 A | 11/2000 | Flom et al. ................. 600/206 |
| 6,142,936 A | 11/2000 | Beane et al. ................ 600/207 |
| 6,254,533 B1 | 7/2001 | Fadem et al. |
| 6,254,534 B1 * | 7/2001 | Butler et al. ................ 600/206 |

FOREIGN PATENT DOCUMENTS

| | | |
|---|---|---|
| EP | 0 950 376 | 10/1999 |
| FR | 1456623 | 9/1966 |
| GB | 1 151 993 | 5/1969 |
| GB | 2 071 502 | 9/1981 |
| GB | 2 255 019 | 10/1992 |
| JP | 10-108868 | 4/1998 |
| WO | WO92/11880 | 7/1992 |
| WO | WO95/07056 | 3/1995 |
| WO | WO95/22289 | 8/1995 |
| WO | WO95/27445 | 10/1995 |
| WO | WO95/27468 | 10/1995 |
| WO | WO 96/36283 | 11/1996 |
| WO | WO 97/32514 | 9/1997 |
| WO | WO 97/32515 | 9/1997 |
| WO | WO98/35614 | 8/1998 |
| WO | WO98/48724 | 11/1998 |
| WO | WO 99/03416 | 1/1999 |
| WO | WO99/25268 | 5/1999 |
| WO | WO99/29250 | 6/1999 |
| WO | WO00/54675 | 9/2000 |
| WO | WO00/54676 | 9/2000 |
| WO | WO00/54677 | 9/2000 |
| WO | WO 01/08563 | 2/2001 |
| WO | WO 01/08581 | 2/2001 |
| WO | WO 00/32116 | 6/2001 |
| WO | WO 00/32117 | 6/2001 |
| WO | WO 00/32119 | 6/2001 |
| WO | WO 00/35356 | 6/2001 |

OTHER PUBLICATIONS

Original Specification of Application No. 09/849,341, filed May 7, 2001.

Original Specification of Application No. 09/801,826, filed Mar. 9, 2001.

Original Specification of Application No. 09/867,593, filed May 31, 2001.

Original Specification of Application No. 09/867,403, filed May 31, 2001.

* cited by examiner

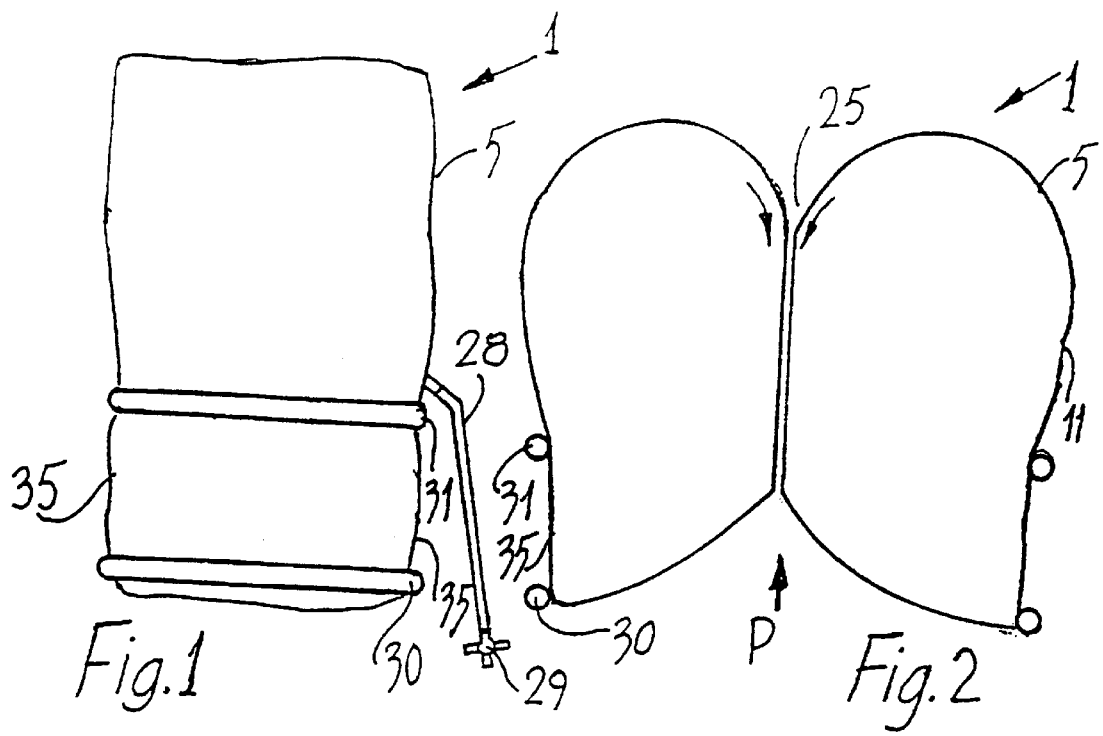
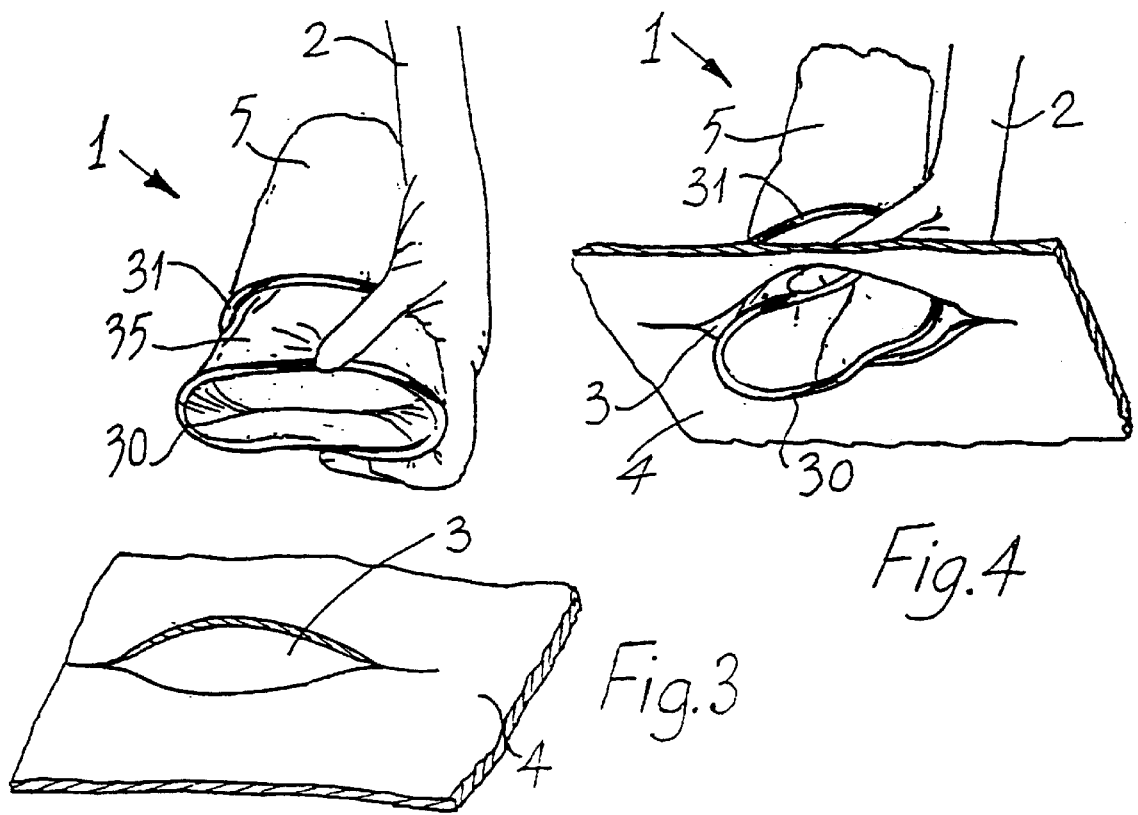

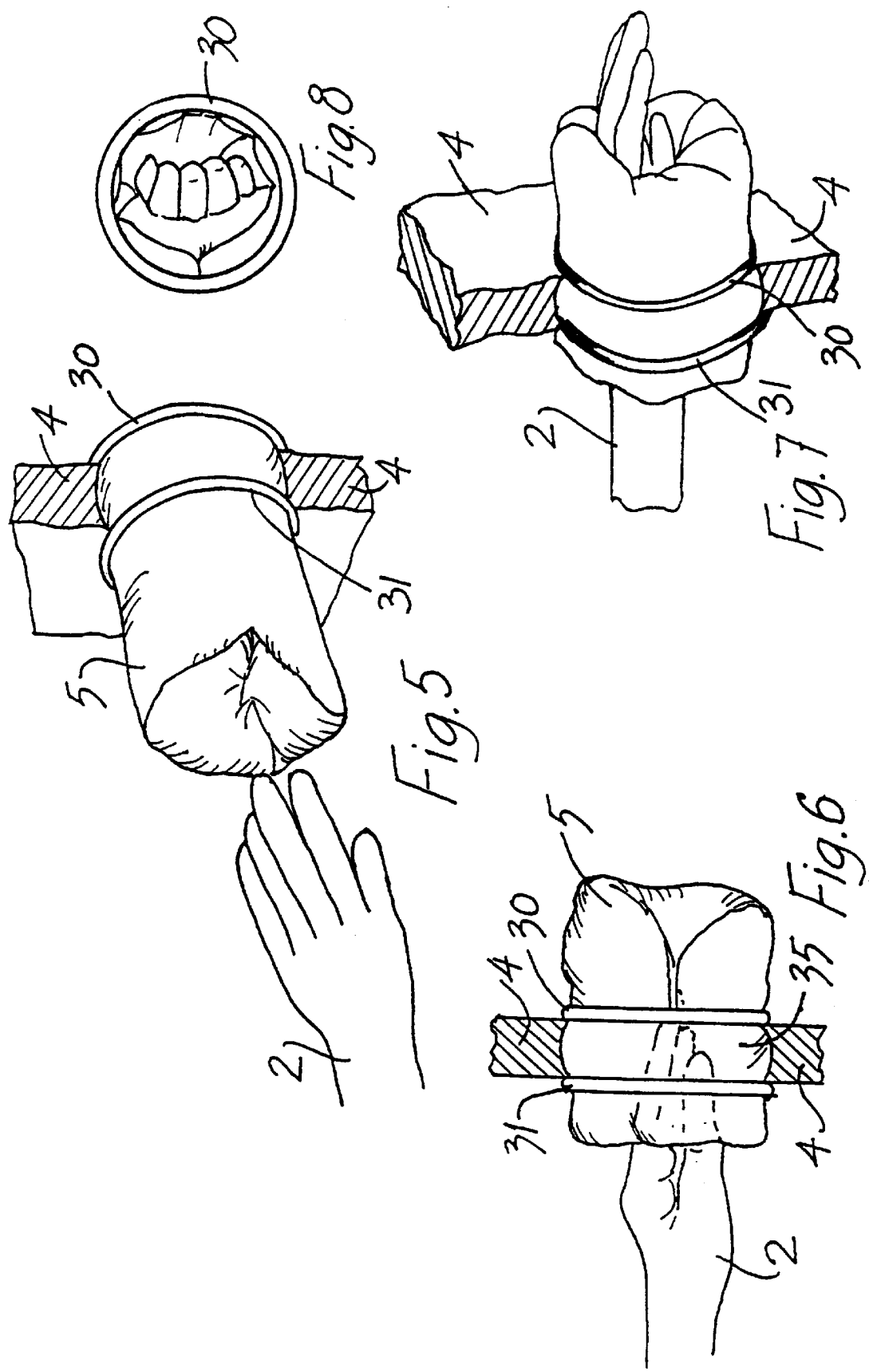

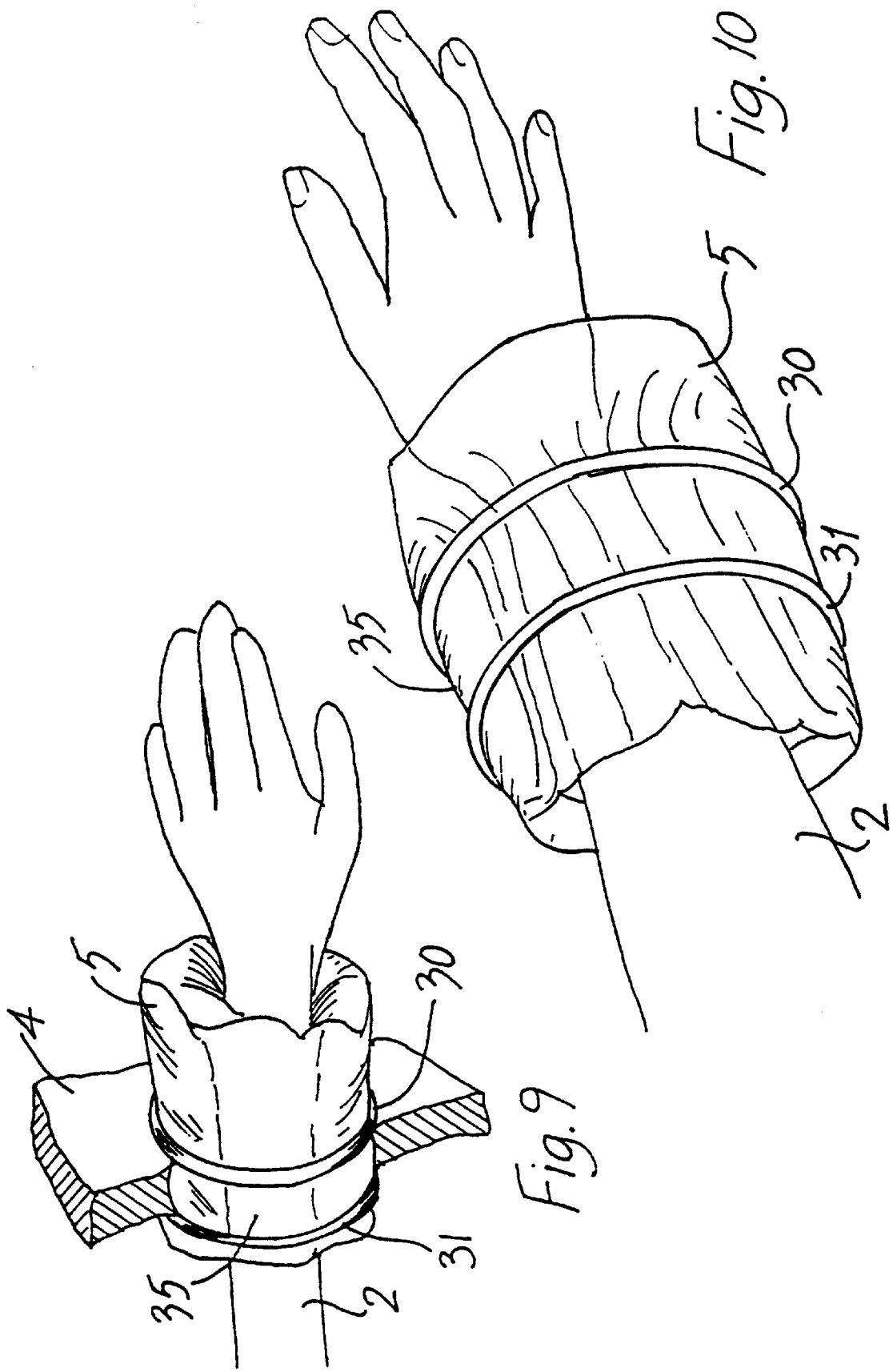

LAPAROSCOPIC SEALED ACCESS DEVICE

This application is a continuation of international application number PCT/IE99/00127, filed Dec. 1, 1999.

The invention relates to a surgical/medical device for laparoscopic surgery to provide surgical access to the abdomen and maintain a gas-tight seal around the arm or an instrument during surgery. Surgery of this type is referred to as hand-assisted laparoscopic surgery or hand-access surgery.

Conventional abdominal surgery requires the creation of an incision in the abdominal wall to allow access to, and visualisation of the internal organs and other anatomical structures. These incisions must be large enough to accommodate the surgeons hands and any instruments to be utilised by the surgeon during the surgery. Traditionally the size of these incisions has been dictated by the need to see, retract and palpate internal bodily structures. While a large incision will provide access to the interior of the abdomen they are associated with longer healing times, are more susceptible to infection and result in unsightly scars.

Alternatives to open surgery exist in the form of endoscopic or laparoscopic surgery. In this method of surgery, the surgeon operates through small incisions using remotely actuated instruments. The instruments pass through the abdominal wall using devices called trocars. These working channels typically have a diameter ranging from 5 to 25 millimeters. Vision is provided using a laparoscope which is typically 20 to 25 centimeters long and uses fibre-optic technology or a CCD camera to provide the operator with a picture of the interior of the abdomen. The abdomen must be insufflated with a gas such as carbon dioxide or nitrogen to maintain a bubble effect and provide a viable working space for the operator to perform the surgery unhindered by the lack of space. This insufflation creates a working space known as the pneumoperitoneum. Trocars through which instruments are inserted are constructed to prevent loss of the gas through them resulting in collapse of the pneumoperitoneum.

The benefits of laparoscopic surgery are numerous. Recovery times have been shown to be reduced due to the absence of a large incision. This has benefits for the patient, the health care organisation and society. The benefits to the patient are reduced stay in hospital, faster mobilisation and return to normal activity. The benefits to the health care organisation is also due to the reduced stay in hospital which is often the most expensive aspect of health care provision. Society benefits in faster return to work and normal activity of the patient.

However, not all surgical procedures can be performed laparoscopically. Surgery requiring the removal of large organ specimens, such as surgery for removal of the colon, has traditionally been hampered by the small incisions used for the introduction of laparoscopic instruments in the surgery.

The other major disadvantages of laparoscopic surgery are due to the complex nature of the technique. Surgeons who wish to practise laparoscopic surgery must spend much time training to master the technique. The success of laparoscopic surgery depends on the skill of the surgeon to manipulate organs and carry out delicate tasks using remotely actuated instruments. Unfortunately in laparoscopic surgery the surgeon is insulated from the material that they are working on. This deprives the surgeon of tactile feedback and the ability to palpate delicate structures. The surgeon's most effective instrument, the hand, is reduced to a device that must simply actuate instruments that are inherently lacking in dexterity and operability due to the constraints on their design placed by the nature of the narrow channels in trocars through which they must pass. Another disadvantage of laparoscopy is that the image viewed by the surgeon is a two dimensional image on a video screen. The surgeon loses three dimensional perspective of depth and distance and awareness of the proximity of other structures during video laparoscopy.

These disadvantages have led to long learning curves for the practitioners of laparoscopic surgery, required highly skilled and coordinated surgical teams and has limited the application of laparoscopic surgery to relatively simple surgical procedures.

Recently, new surgical techniques have been developed that combine the advantages of both open surgery and laparoscopic surgery. In these new techniques surgery is carried out using a laparoscopic approach with the addition of a slightly larger incision to allow the surgeon to insert a hand into the insufflated abdomen. This is often referred to as hand-assisted laparoscopic surgery or HALS.

HALS allows surgeons to regain the tactile feedback and three-dimensional perspective lost in the conversion from open to laparoscopic procedures. It also permits rapid finger dissection, enhanced retraction capabilities and simplified haemostasis. There are several publications in the literature describing procedures carried out using a hand-assisted approach. These include total and sub-total colectomy, rectopexy, Nissen's fundoplication, gastrectomy, splenectomy, nephrectomy, pancreatectomy and others. Some of these procedures were previously performed using an open technique only. Over the past few years several centres have been investigating HALS with surgical device companies and increasing the literature on the subject. With the advent of surgical devices for facilitating HALS it is expected that more open surgical procedures will be converted to HALS procedures.

The key to the success of hand-assisted laproscopic surgery is to provide that seals to the wound edge and to a surgeons arm to maintain the pneumoperitoneum required. The device should provide freedom of movement including rotational, lateral and translational; In addition it should be possible to use laparoscopic instruments with the device.

Various hand access devices have been proposed however, to date, no hand access device is available that adequately addresses these key issues.

U.S. Pat. No. 5,366,478 (Brinkerhoff et al) describes a device which is said to be for use during endoscopic surgery, the device having two inflatable toroidal sections connected by a transitional section. The transitional section is said to function to allow the passage of air from one toroid to the other toroid on inflation of the device. Each toroidal section contains a flexible stiffening ring. The stiffening ring in the outer toroid is illustrated in a position floating above the abdominal wall after inflation. It is unclear how this stiffening ring maintains this configuration. It is therefore unlikely that this device will operate as described. Also it is difficult to pass an object such as a surgeon's forearm through a lumen in the transitional section, because of frictional resistance to the movement of the object relative to the transitional section.

A medical device for forming an external extension of the pneumoperitoneum is described in U.S. Pat. No. 5,480,410 (Cuschieri et al). The device includes an enclosure sealed into a trocar puncture site in an abdominal wall. Insufflation gas passes from the body cavity into the enclosure inflating it. A number of valved openings are provided on the device to enable access to the enclosure interior.

In U.S. Pat. No. 5,514,133 (Golub et al) describes an endoscopic surgical apparatus, which enables a surgeon to access a surgical site through an opening. The apparatus includes two plates, which engage the outer and inner surfaces of the abdominal wall, and a sealing member, which inhibits the flow of gas through the opening. The seal in this apparatus does not maintain complete insufflation of the body cavity, gas can gradually leak out through the flap-valves and seal. The valve configuration also makes it impossible to extracorporealise an organ, which is preferred in hand assisted surgery devices. The device also has a complicated construction.

A surgical glove suitable for endoscopic surgical procedures is disclosed in U.S. Pat. No. 5,526,536 (Cartmill). The glove has an inflatable wrist section, which when inflated, provides a seal between the surgeon's hand and the body wall. The surgeon's gloved hand must remain in the body cavity to maintain insufflation of the body cavity. Therefore this device also restricts the actions of the surgeon.

U.S. Pat. No. 5,522,791 (Leyva), describes an abdominal retractor, which retracts an abdominal incision providing access for a hand into a body cavity. The hand is passed into a sleeve and sealed therein, the other end of the sleeve being mounted to the retractor.

Devices for sealing a surgical incision while providing access for a surgeon's hand are also known. For example, a method of performing laparoscopic surgery is described in U.S. Pat. No. 5,636,645 (Ou), which includes the steps of inserting a surgeon's gloved hand into a body cavity and sealing the hand to body tissue surrounding the cavity. This method restricts the actions of the surgeon because the surgeon's gloved hand must remain in the body cavity sealed to the surrounding tissue to maintain insufflation of the body cavity. The seal between the surgeon's gloved hand and the surrounding tissue must be reestablished each time the gloved hand is inserted into the body cavity, if insufflation of the body cavity is to be maintained.

An apparatus and a method for carrying out minimally invasive laparoscopic surgery is also described in U.S. Pat. No. 5,640,977 (Leahy et al). A surgeon's hand is passed through a sleeve to access a body cavity, the sleeve being sealed around the surgeon's forearm.

U.S. Pat. No. 5,653,705 (de la Torre et al) discloses an envelope, which provides access for an object passing into a body tissue incision, while maintaining insufflation of the body cavity. A first opening in the envelope is sealed around the body tissue incision and a second opening is sealed around an object passed into the envelope.

Devices for use during surgery which provide access to a surgical site and effect a seal independent of a surgeon's hand are also known. In general devices of this type are positioned predominantly external to a body cavity, and are complex, large and bulky. These devices prove difficult to use because they are cumbersome and/or because of their complexity. For example, a flexible, fluid-tight envelope which provides access for an object passing through a body tissue incision while maintaining insufflation pressure is described in U.S. Pat. No. 5,672,168 (de la Torre et al). This is a complex device including a first opening secured and sealed to the body tissue incision, and a second opening distal from the body tissue incision and sealed to a surgeon's forearm. The device also includes a housing containing a valve element at the body tissue incision.

An access port device for use during a surgical procedure is described in U.S. Pat. No. 5,803,921 (Bonadio). An object is passed into the device sleeve, the device is sealed around the object at the sleeve opening and the device is also sealed at the body cavity. The seals maintain insufflation of the patient's body cavity. However it may be difficult to pass an object through the access port device and into the body cavity because of frictional resistance to the movement of the object relative to the device sleeve. An adhesive flange is required to stick to the abdominal wall. This is not very effective and can become undone due to the presence of moisture around the wound edge. The device provides no retraction force and the walls of the incision are displaced only when an object is inserted through it. The feathered valve is not an effective means of sealing and there may be leakage insufflation gas.

U.S. Pat. No. 5,741,298 (MacLeod) describes a method for performing surgery using a multi-functional access port. The access port has a sealing ring which protects the body wall incision from contamination. A sealing cap or a surgical glove is connected to the sealing ring to maintain insufflation of the body cavity. This surgical method is also restrictive because the surgeon's gloved hand must remain sealed to the sealing ring, if body cavity insufflation is to be maintained.

A surgical apparatus for use during hand assisted minimally invasive surgery is described in U.S. Pat. No. 5,813,409 (Leahy et al). A sleeve is mounted at one end to a body tissue incision. The sleeve seals to the surgeon's hand to maintain pneumpperitoneum. Surgical instruments may then be passed into the sleeve to a surgeon's hand within, which may then be inserted into the incision. This device requires a multistep process for installation and comes in several parts. The device takes up a large amount of space on the abdomen and the application of the wound-retractor component is cumbersome.

U.S. Pat. No. 5,906,577 (Beane et al) describes a retractor device for retracting the edges of an incision to form an opening to a body cavity. A flexible sleeve is mounted to the retractor, and an object passed through the device is sealed to maintain insufflation of the body cavity. This device also consists of many component parts that must be assembled carefully. The device has a very constricting and uncomfortable seal to the arm. The retraction mechanism can pop out easily, causing complete loss of pneumoperitoneum, making the device disadvantageous. It also has a large abdominal footprint.

WO 98/35615 (Crook) describes a device for performing HALS that consists of a wound-edge retractor to which is attached a sleeve similar to others mentioned above. This device also consists of several component parts and has a complicated installation procedure.

Generally known devices are difficult to use because they are cumbersome and/or because of their complexity.

U.S. Pat. No. 5,545,179 (Williamson) describes an access assembly, which provides access for surgical instruments to a body cavity during surgery and seals the instruments passing into the body cavity. A sealing sleeve is inflated to form a large balloon portion within the body cavity, the balloon portion being constrained to remain within the body cavity. Therefore it is difficult to retract a surgical instrument through the balloon portion of the assembly and out of the body cavity, because of frictional resistance to the movement of the surgical instrument relative to the balloon sleeve.

An access port device for use during hand-assisted laparoscopic surgery is described in JP 10-108868 (Tamai, Shitomura). This single-piece device consists of a wound retractor component to which is attached an iris valve. The wound retractor component is made of two rings, an inner ring and an outer ring joined by a silastic sleeve to provide a retractive force. The device is inserted into an incision and the surgeon's hand may be inserted through the device. The iris valve is then closed around the arm to effect a seal to prevent the escape of insufflation gas. Due to the nature of the inner ring and the silastic sleeve the device may be easily dislodged. The iris valve is not an effective seal, especially during lateral movement of the surgeon's arm. In addition the device does not facilitate translation movement or reach because of the seal of the iris valve.

There is therefore a need for a sealing device, which provides effective sealing means to seal an object passing through the device, and which is convenient and easy to use, compact and neat, and may be used repetitively with minimum delay and minimum effort.

STATEMENTS OF INVENTION

According to the invention there is provided a surgical access device for use in laproscopic surgery through an opening comprising:

a sleeve of pliable material, the sleeve having an outer sleeve section and an inner sleeve section;

a chamber for pressurised fluid defined between the inner and outer sleeve sections;

the inner sleeve section defining a lumen for receiving an object such as a surgeons arm or an instrument therein;

the sleeve being evertable on engagement of an object in the lumen and axial movement relative thereto so that the inner sleeve section is rolled over outwardly to become an outer sleeve section and the outer sleeve section is correspondingly rolled over inwardly to become an inner sleeve section; and at least one eversion limiting means to limit the eversion of the sleeve into an opening.

In one embodiment of the invention the sleeve is axially turned back on itself to define the outer sleeve section and the inner sleeve section.

In a particularly preferred embodiment the nominal diameter of the outer sleeve section is the same as the diameter of the inner sleeve section.

The chamber is preferably fluid impermeable. Ideally the chamber has a port for inflation of the chamber.

In one embodiment of the invention the device includes a first eversion limiting means for location externally of the opening and a second eversion limiting means for location internally of the opening.

Preferably the or each eversion limiting mean is an O-ring.

The O-ring is of a resilient material.

In one embodiment the or each eversion limiting means is housed in the chamber. In this case preferably the or each eversion limiting means is movable axially in the chamber.

In one embodiment there are two eversion limiting means and both are independently movable in the chamber.

In another embodiment there are two eversion limiting means and a linkage means is provided between them. The linkage means may be of pliable material. Preferably the linkage means comprises a linkage sleeve.

In one embodiment the device includes a sealing means to seal an object to be passed through the access opening. The sealing means may preferably comprise a glove to receive a surgeons hand and/or forearm. Preferably sealing means is attached to the sleeve.

BRIEF DESCRIPTION OF THE DRAWINGS

The invention will be more clearly understood from the following description thereof given by way of example only with reference to the accompanying drawings, in which:

FIG. 1 is a perspective view of a hand access device according to the invention;

FIG. 2 is a cross sectional view of the device of FIG. 1;

FIGS. 3 and 4 are a perspective views of the device being inserted into an incision in an abdominal wall;

FIG. 5 to 7 are perspective, partially cross sectional views of a surgeons hand being inserted through the device;

FIG. 8 is a distal end view of the device with a hand in place;

FIG. 9 is a perspective, partially cross sectional view of the hand access device with a surgeons hand fully inserted;

FIG. 10 is a perspective view of the device in an intermediate position on a surgeon's arm;

DETAILED DESCRIPTION

Figure 11:
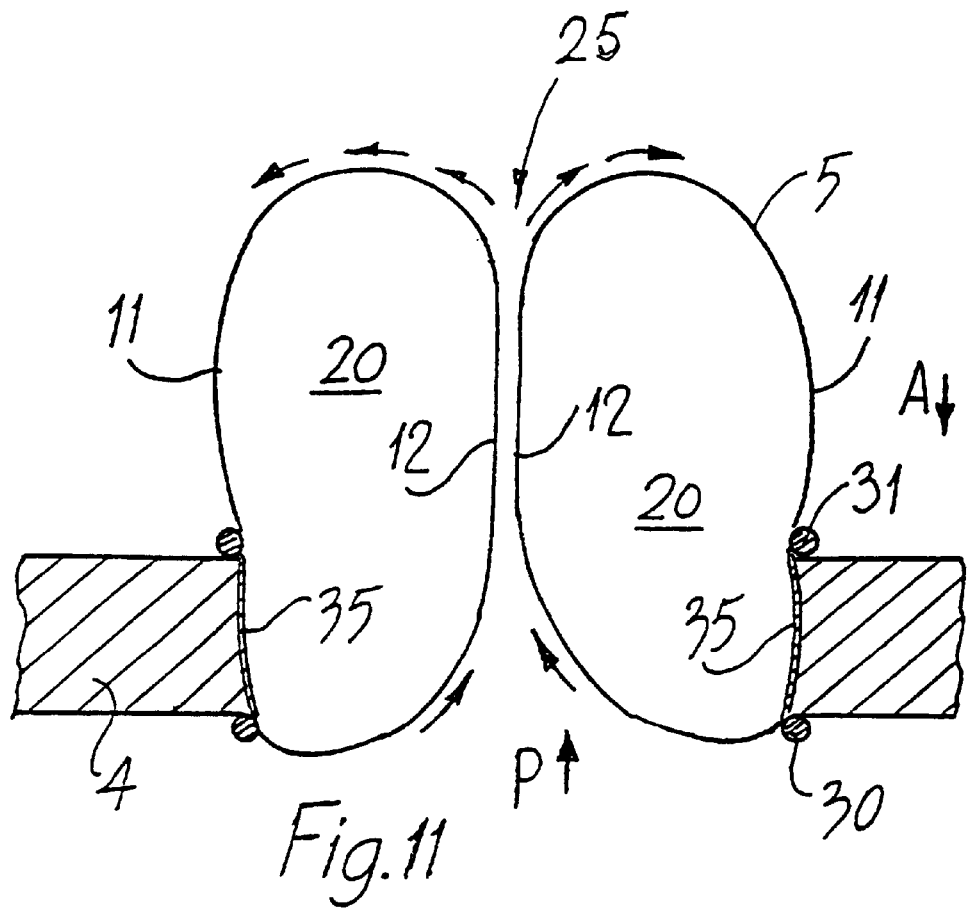
FIG. 11 is a cross sectional view of the device of FIGS. 1 to 10 in position ready to receive a surgeon's arm.
Figure 12:
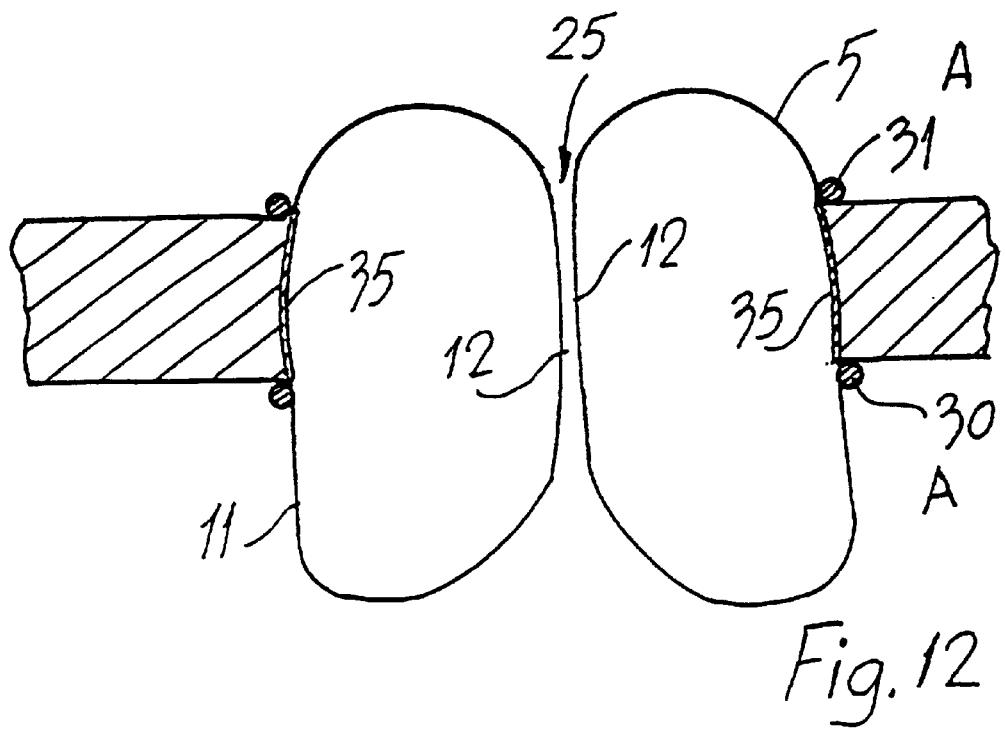
FIG. 12 is a cross sectional view similar to FIG. 11 with the device inserted through an incision.

Referring to the drawings and initially to FIGS. 1 to 13 there is illustrated a hand access device 1 according to the invention for use as a seal for sealing a surgeon's forearm 2 on entry through a wound opening 3, for example in an abdominal wall 4.

The device 1 comprises a substantially tubular sleeve 5 of pliable gas tight material formed from a tube of a suitable biocompatible plastics material. The tube is turned axially back on itself to define an outer sleeve section 11 and an inner sleeve section 12.

The inner and outer sleeve sections 11, 12, define therebetween a sealed inflatable chamber 20. The inner sleeve section 12, defines a lumen 25 and, on inflation of the chamber 20, the inner sleeve section 12 engages an object extending or passing through the lumen 25.

The hand access device includes an eversion limiting means for the sleeve 5. The eversion limiting means is in this case provided by a first O-ring 30, which is attached to the sleeve 5 and a second O-ring 31, which is attached to an axially spaced-apart location on the sleeve 5. The inner O-ring 30 is of a suitable resilient elastomeric material for bunching of the ring 30 to facilitate ease of insertion into a wound 3 as illustrated in FIGS. 3 and 4.

As a surgeon inserts his forearm 2 through the lumen 25 of the device 1, the inner sleeve section rolls 12 along with the arm 2 and in turn the outer sleeve section 11 everts. An seal is maintained around the surgeon's forearm 2 and the sealed integrity of the body cavity being operated upon is substantially maintained. To facilitate insertion of the surgeon's arm 2 lubrication may be used. The device 1 and may be inflated prior to or during use through a suitable inflation line 28 fitted with a valve 29.

A wound protector section 35 of the sealing device between the rings 30, 31 may be of a plastics sheet material that has a greater flexibility than that of the main body of the sleeve 5. In this way, on inflation of the sleeve 5 the protector section 35 stretches to conform closely to the irregular shape of the wound 3 and provide a tight seal to the wound opening 3. In addition, the inner ring 30 is drawn against the inner wall surrounding the wound 3, on inflation of the sleeve 5. The arrangement also facilitates lubricated rotation of the protector section 35 which facilitates insertion of a surgeon's arm 2.

The inner O-ring 30 may have a larger diameter than that of the outer O-ring 31 to create a tapering effect. This arrangement promotes a pressure differential which assists insertion of a surgeon's arm 2 acting against the internal abdominal pressure.

The invention provides a device which allows laparoscopic surgeons insert their hand into the abdominal space during laparoscopic surgery and to regain the tactile feedback, three dimensional perspective and general use of the hand as an operative tool as it was in open surgery. The device is easy to insert into a small incision and easy to withdraw from the same incision. The device facilitates ease of movement within the device so that the device is not a hindrance to the performance of the surgery. A seal is provided to both the operator's forearm and to the wound edges so as to substantially prevent the escape of gases used to maintain the pneumoperitoneum.

In addition the device allows the removal of organ specimens from the abdominal cavity through the device for the purpose of either removing them completely from the body or for performing a surgical procedure on them while they are temporarily removed from the body or extracorporealised. The invention allows an operator to remove the hand from the device and leave the device in place while substantially maintaining the pneumoperitoneum.

The device consists of a double-layer polymeric sleeve through which the operator can extend his hand into the abdomen. The device is held in place in the abdominal incision by an arrangement of rings attached to the outer layer of the sleeve and extending around the outer layer of the sleeve. The purpose of the rings is to provide an anchorage for the polymeric sleeve when it is in the abdominal incision. A stopcock valve and inflation bulb allow the device to be inflated when it is in position in the incision.

When the device is in its correct position and is inflated the lumen substantially closes and the device seals up against the edges of the incision, thus substantially preventing the escape of gas from the pneumoperitoneum to the exterior either through the device or between the device and the edges of the incision. If the operator's hand is within the sleeve when it is inflated, the lumen will close around the arm and effect a seal. The operators hand need not be within the device when it is inflated. The operator's hand may be inserted into the abdominal cavity through the device after it has been inflated.

The access device may be used for insertion of an instrument which may be of any suitable cross section such as circular or square.

Figure 13:
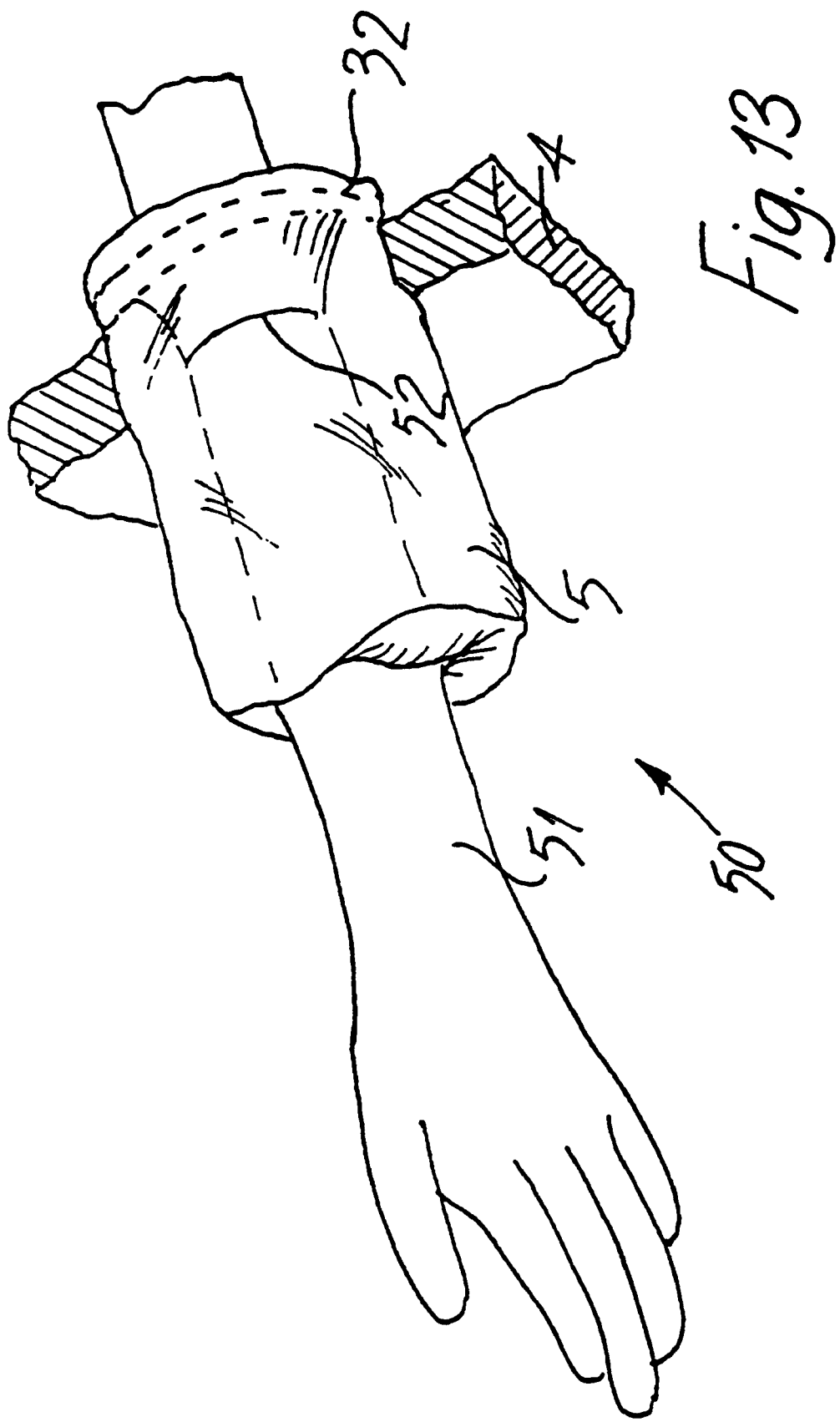
FIG. 13 is a perspective, partially cut-away view of another hand access device of the invention.

Referring to FIG. 13 there is illustrated another hand access device 50 which is similar to the device described above and like parts are assigned the same reference numerals. In this case a surgical glove 51 is attached to the sleeve 5, for example by a heat welded seam 52. This enhances the seal to the surgeons arm as the seam 52 prevents egress of gas. The glove 51 may be of any suitable material which may be stretchable and/or pliable. In this case only an outer eversion limiting ring 31 is provided.

Figure 14:
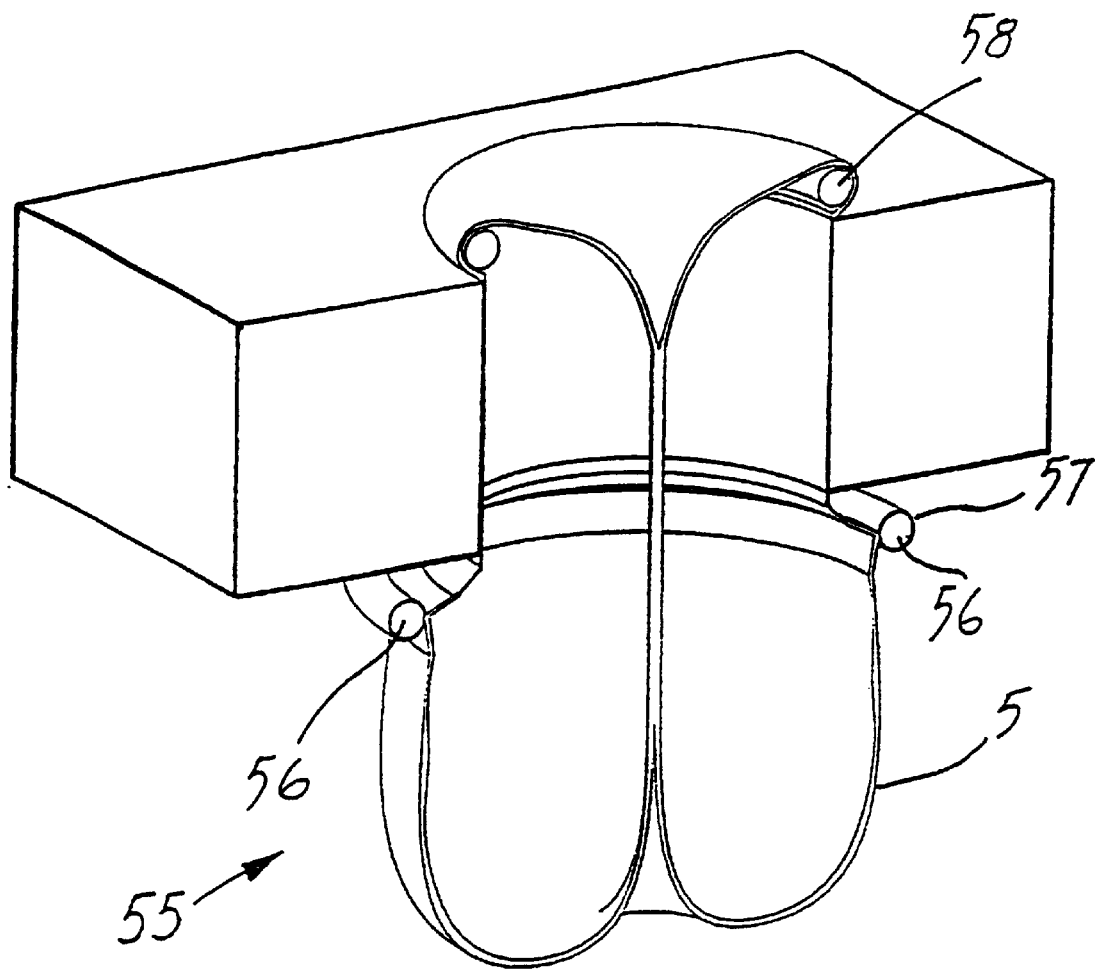
FIG. 14 is a perspective, partially cut-away view of a further hand access device of the invention, in use.

Referring to FIG. 14 there is illustrated a modified hand access device 55 according to the invention. In this case an inner ring 56 is enclosed in a pocket 57 on the sleeve 5 while an outer ring 58 is free to move between the walls of the sleeve.

Figure 16:
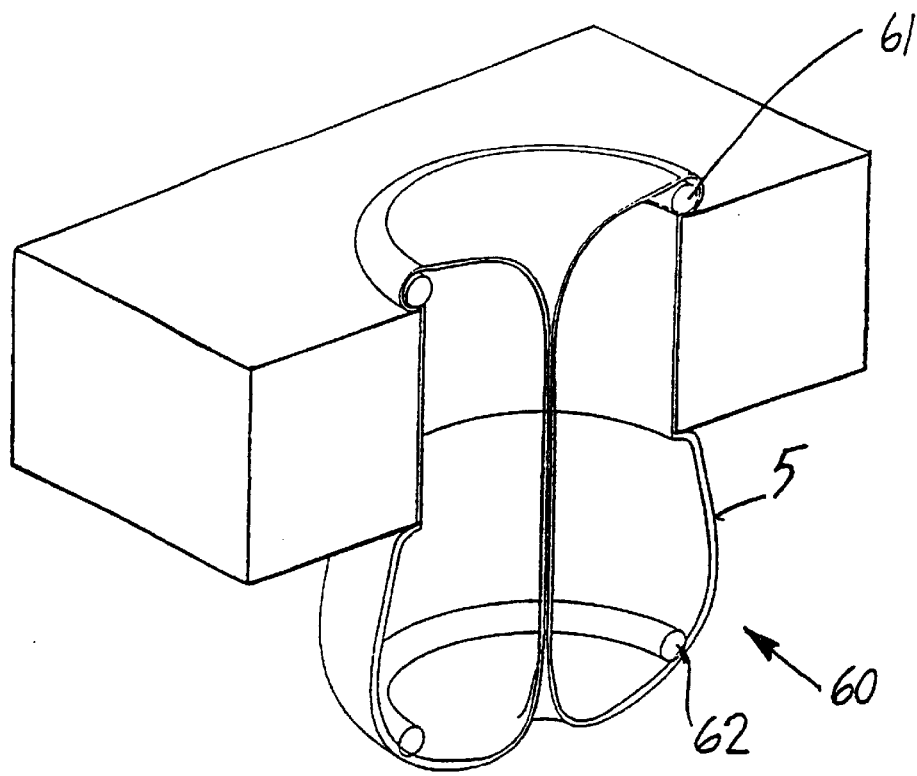
FIG. 16 is a view of the device of FIG. 15, in use.
Figure 15:
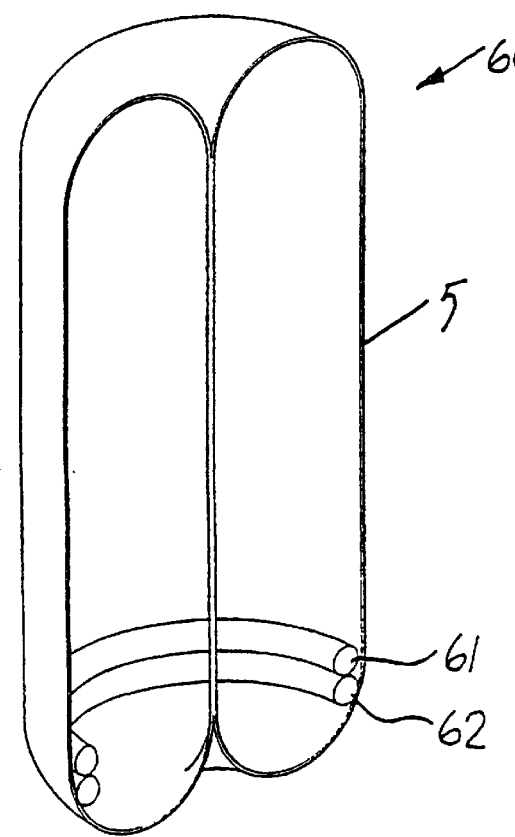
FIG. 15 is a perspective, partially cut-away view of another hand access device of the invention.

Referring to FIGS. 15 and 16 there is illustrated another hand access device 60 in which eversion limiting rings 61, 62 are free to move axially inside the sleeve 5. The device is used as described above, the outer ring 61 engaging the outside of the abdominal wall on insertion to limit eversion into the incision. The inner ring 62 is free between the walls of the sleeve 5 when the sleeve is fully everted into the wound as illustrated in FIG. 16. On withdrawal of a surgeons arm eversion of the sleeve outwardly is limited by engagement of the ring 62 against the inside of the abdominal wall. One advantage of this arrangement is that the same device may be used for a wide range of different thicknesses of abdomen.

Figure 18:
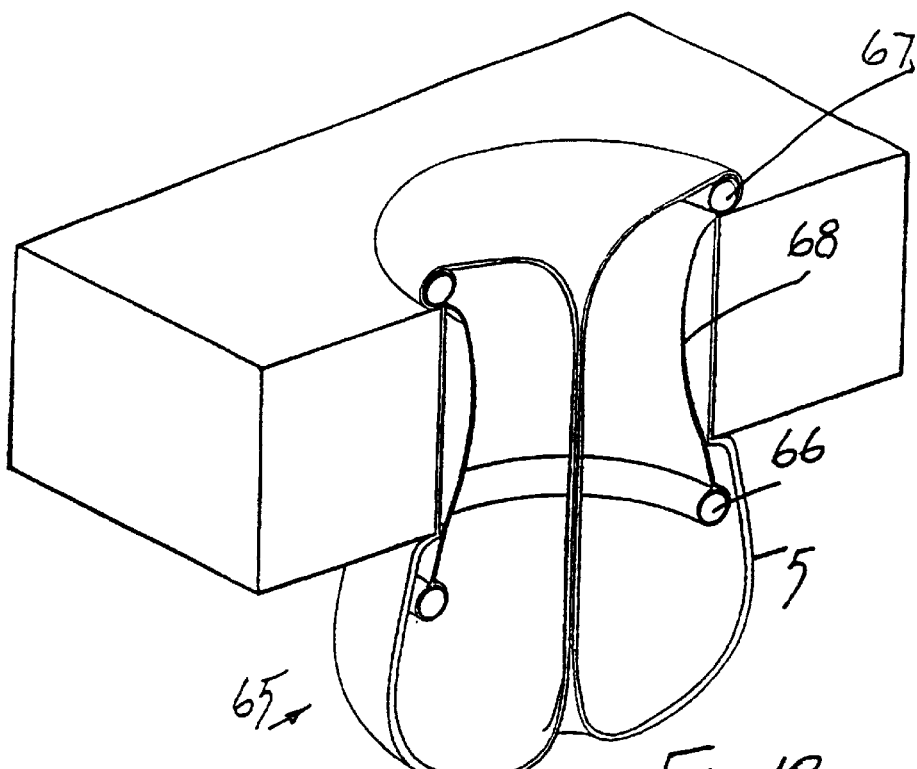
FIG. 18 is a view of the device of FIG. 17, in use.
Figure 17:
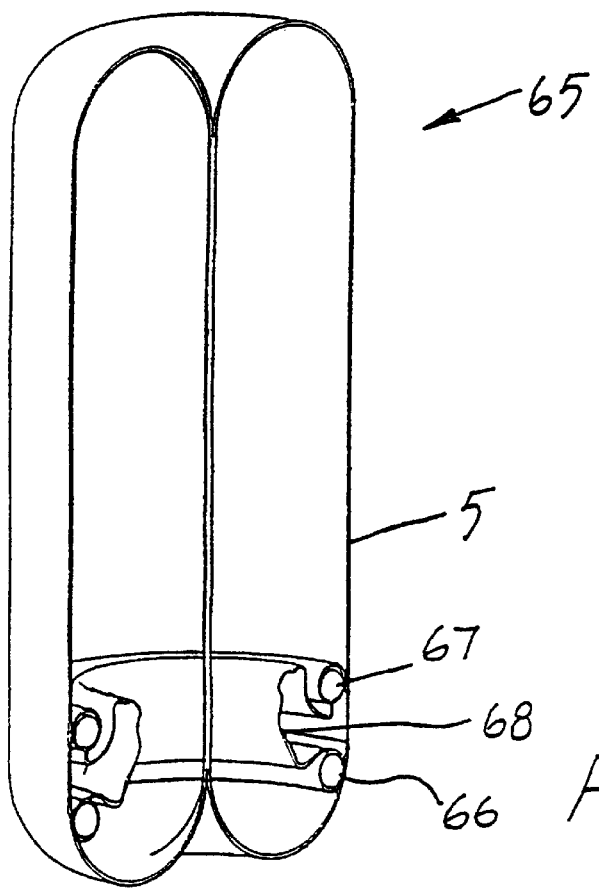
FIG. 17 is a perspective, partially cut-away view of a further hand access device of the invention.

Referring to FIGS. 17 and 18 there is illustrated another hand access device 65 which is again similar to those described above. In this case inner and outer rings 66, 67 are not attached to the sleeve 5, however a linking section 68 of pliable material extends between the rings 66, 67.

Figure 20:
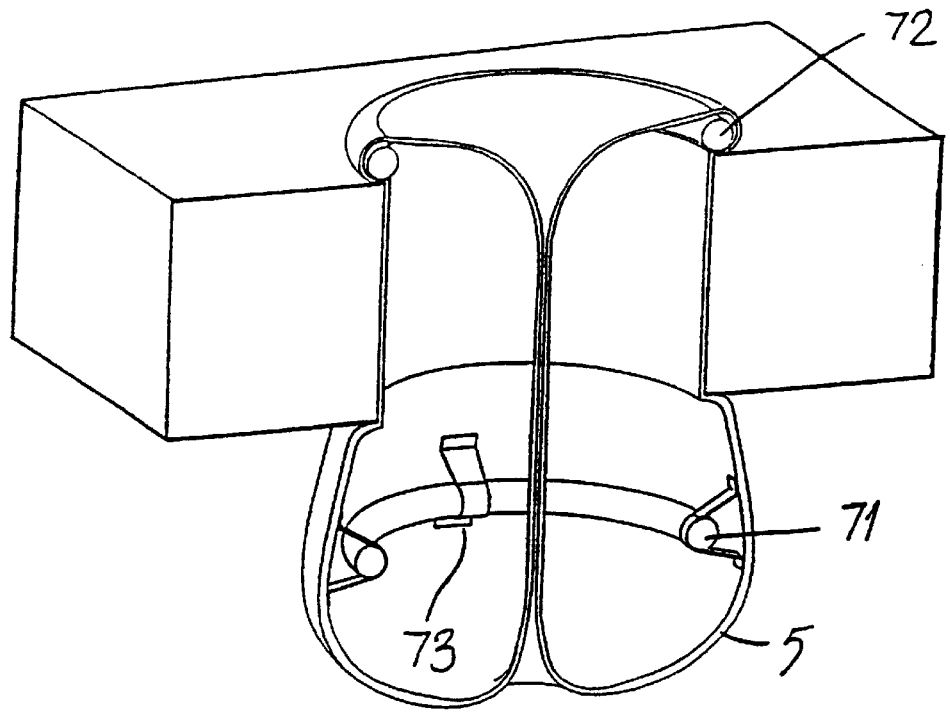
FIG. 20 is a view of the device of FIG. 19, in use.
Figure 19:
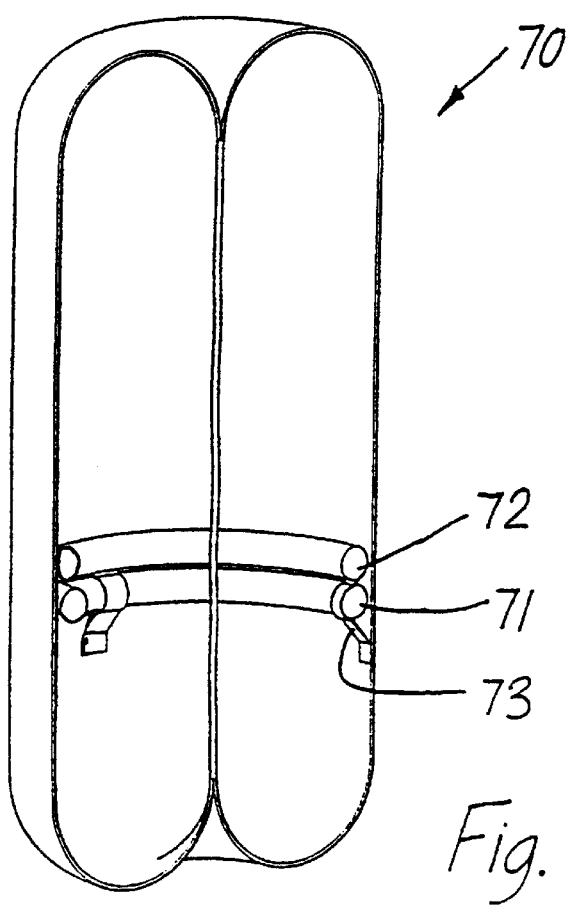
FIG. 19 is a perspective, partially cut-away view of a still further hand access device of the invention.

Referring now to FIGS. 19 and 20 there is illustrated another hand access device 70 according to the invention. In this case an inner ring 71 is held in a desired axial position in the sleeve 5 by adhesive tapes 73. An outer ring 72 is free to move axially within the sleeve.

Reference is also made to appropriate alternatives and modifications which are outlined in our parallel applications referenced ATRO1/C, ATRO12/C, ATRO14/C/, ATRO15/C, ATRO16/C/, the entire contents of which are incorporated herein by reference.

The invention is not limited to the embodiments hereinbefore described which may be varied in construction and detail.

What is claimed is:

1. A medical sealing device for engaging an incision in a patient, comprising:
   a sleeve comprising an incision engagable wall section, a movable wall section, an inflation space, and a longitudinal axis; and
   a ring located at at least one end portion of the movable wall section for assisting in maintaining the sleeve against a wall of the incision,
   the movable wall section movable relative to the incision engagable wall section and forming at least a central lumen extending along the longitudinal axis, inflation of the inflatable space urging the central lumen into a sealed position;
   the movable wall section assisting in the sealing of an object extending through the lumen and movable upon engagement and axial movement of the object with the lumen by eversion so that a part of an inner portion of the sleeve moves to become a part of an outer portion of the sleeve and a section of the outer portion of the sleeve moves to become a section of the inner portion of the sleeve; and
   wherein said ring comprises a first ring located at a distal end portion of the movable wall section, and the sealing device further comprises a second ring located at a proximal end portion of the movable wall section, each said first and second rings assisting in positioning the sleeve about the incision and orientated to lie in a plane that is generally perpendicular to the longitudinal axis of the sleeve.

2. A medical sealing device according to claim 1, wherein the second ring is axially movable in relation to the sleeve.

3. A medical sealing device according to claim 2, wherein the second ring is located within the inflation space.

4. A medical sealing device according to claim 1, wherein the first and second rings are fixedly coupled to the sleeve outside of the inflation space.

5. A medical sealing device according to claim 4, wherein the first and second rings are fixedly coupled to the sleeve within the inflation space.

6. A medical sealing device according to claim 1, wherein the sleeve is formed of a pliable material.

7. A medical sealing device according to claim 1, wherein the incision engagable wall section is formed of a material different than the material forming the movable wall section.

8. A medical sealing device according to claim 1, wherein the incision engaging wall section has approximately the same diameter as the movable wall section if measured when the inflation space is uninflated.

9. A medical sealing device according to claim 1, wherein the lumen of the movable wall section comprises a diameter smaller than a minimum diameter of an object to be received or passed through the lumen, the diameter of the lumen being measured when the inflation space is fully inflated.

10. A medical sealing device according to claim 1, further comprising an access port to the inflation space for assisting in an inflation of the inflation space.

11. A medical sealing device for engaging an incision in a patient, comprising:
a sleeve comprising an incision engagable wall section, a movable wall section, an inflation space, and a longitudinal axis; and
a ring located at at least one end portion of the movable wall section for assisting in maintaining the sleeve against a wall of the incision,
the movable wall section movable relative to the incision engagable wall section and forming at least a central lumen extending along the longitudinal axis, inflation of the inflatable space urging the central lumen into a sealed position;
the movable wall section assisting in the sealing of an object extending through the lumen and movable upon engagement and axial movement of the object with the lumen by eversion so that a part of an inner portion of the sleeve moves to become a part of an outer portion of the sleeve and a section of the outer portion of the sleeve moves to become a section of the inner portion of the sleeve; and
wherein said ring comprises a first ring located at a proximal end of the movable wall section and axially movable in relation to the sleeve, and the sealing device further comprises a second ring fixedly secured at a distal end portion of the movable wall section, each said first and second rings assisting in positioning the sleeve about the incision and orientated to lie in a plane that is generally perpendicular to the longitudinal axis of the sleeve.

12. A medical sealing device according to claim 11, wherein the first and second rings each comprise flexible O-rings.

13. A medical sealing device for engaging an incision in a patient, comprising:
a sleeve comprising an incision engagable wall section, a movable wall section, an inflation space, and a longitudinal axis; and
a ring located at at least one end portion of the movable wall section for assisting in maintaining the sleeve against a wall of the incision,
the movable wall section movable relative to the incision engagable wall section and forming at least a central lumen extending along the longitudinal axis, inflation of the inflatable space urging the central lumen into a sealed position;
the movable wall section assisting in the sealing of an object extending through the lumen and movable upon engagement and axial movement of the object with the lumen by eversion so that a part of an inner portion of the sleeve moves to become a part of an outer portion of the sleeve and a section of the outer portion of the sleeve moves to become a section of the inner portion of the sleeve; and
wherein said ring comprises a first ring and the sealing device comprises a second ring, the first and second rings being located within the inflation space axially spaced from each other, and each lying in a plane generally perpendicular to the longitudinal axis of the sleeve.

14. A medical sealing device according to claim 13, wherein the first and second rings are each independently axially movable in relation to the sleeve.

15. A medical sealing device according to claim 13, wherein the first and second flexible rings are coupled to each other and together axially moveable in relation to the sleeve.

16. A medical sealing device for engaging an incision in a patient, comprising:
a sleeve comprising an incision engagable wall section, a movable wall section, an inflation space, and a longitudinal axis; and
a ring located at at least one end portion of the movable wall section for assisting in maintaining the sleeve against a wall of the incision,
the movable wall section movable relative to the incision engagable wall section and forming at least a central lumen extending along the longitudinal axis, inflation of the inflatable space urging the central lumen into a sealed position;
the movable wall section assisting in the sealing of an object extending through the lumen and movable upon engagement and axial movement of the object with the lumen by eversion so that a part of an inner portion of the sleeve moves to become a part of an outer portion of the sleeve and a section of the outer portion of the sleeve moves to become a section of the inner portion of the sleeve;
wherein the incision engagable wall section is formed of a material different than the material forming the movable wall section; and
wherein the incision engagable wall section is formed of a material more flexible than the material forming the movable wall section.

17. A medical sealing device for engaging an incision in a patient, comprising:
a sleeve comprising an incision engagable wall section, a movable wall section, an inflation space, and a longitudinal axis; and
a ring located at a proximal end portion of the movable wall section for assisting in maintaining the sleeve against a wall of the incision, said ring being axially movable in relation to the sleeve,
the movable wall section movable relative to the incision engagable wall section and forming at least a central lumen extending along the longitudinal axis, inflation of the inflatable sleeve urging the central lumen into a sealed position;

the movable wall section assisting in the sealing of an object extending through the lumen and movable upon engagement and axial movement of the object with the lumen by eversion so that a part of an inner portion of the sleeve moves to become a part of an outer portion of the sleeve and a section of the outer portion of the sleeve moves to become a section of the inner portion of the sleeve; and wherein said ring comprises a first ring and the sealing device further comprises a second ring that is coupled to the sleeve.

18. A medical sealing device according to claim 17, wherein at least one of the first and second rings comprises a flexible O-ring.

19. A medical sealing device according to claim 17, wherein said first and second ring each comprise a flexible O-ring.

20. A medical sealing device according to claim 17, wherein the sleeve is formed of a pliable material.

21. A medical sealing device according to claim 17, wherein the incision engagable wall section is formed of a material different than the material forming the movable wall section.

22. A medical sealing device according to claim 17, wherein the incision engaging wall section has approximately the same diameter as the movable wall section if measured when the inflation space is uninflated.

23. A medical sealing device according to claim 17, wherein the lumen of the movable wall section comprises a diameter smaller than a minimum diameter of an object to be received or passed through the lumen, the diameter of the lumen being measured when the inflation space is fully inflated.

24. A medical sealing device according to claim 17, further comprising an access port to the inflation space for assisting in an inflation of the inflation space.

25. A medical sealing device for engaging an incision in a patient, comprising:

a sleeve comprising an incision engagable wall section, a movable wall section, an inflation space, and a longitudinal axis; and a ring located at a proximal end portion of the movable wall section for assisting in maintaining the sleeve against a wall of the incision, said ring being axially movable in relation to the sleeve, the movable wall section movable relative to the incision engagable wall section and forming at least a central lumen extending along the longitudinal axis, inflation of the inflatable sleeve urging the central lumen into a sealed position;

the movable wall section assisting in the sealing of an object extending through the lumen and movable upon engagement and axial movement of the object with the lumen by eversion so that a part of an inner portion of the sleeve moves to become a part of an outer portion of the sleeve and a section of the outer portion of the sleeve moves to become a section of the inner portion of the sleeve;

wherein the incision engagable wall section is formed of a material different than the material forming the movable wall section; and wherein the incision engagable wall section is formed of a material more flexible than the material forming the movable wall section.

* * * * *